US00PP34622P2

(12) United States Plant Patent
Stoppel

(10) Patent No.: US PP34,622 P2
(45) Date of Patent: Oct. 4, 2022

(54) SWEET CHERRY TREE NAMED 'PRIM 41'

(50) Latin Name: ***Prunus avium* (L.) L.**
Varietal Denomination: Prim 41

(71) Applicant: Cerasina GmbH, Kressbronn (DE)

(72) Inventor: Peter Stoppel, Kressbronn (DE)

(73) Assignee: Cerasina GmbH, Kressbronn (DE)

( * ) Notice: Subject to any disclaimer, the term of this patent is extended or adjusted under 35 U.S.C. 154(b) by 0 days.

(21) Appl. No.: 17/803,075

(22) Filed: Feb. 2, 2022

(51) Int. Cl.
*A01H 5/08* (2018.01)
*A01H 6/74* (2018.01)

(52) U.S. Cl.
USPC ..... Plt./181

(58) Field of Classification Search
USPC ..... Plt./181, 183
See application file for complete search history.

*Primary Examiner* — Susan McCormick Ewoldt
(74) *Attorney, Agent, or Firm* — Myers Bigel, P.A.

(57) ABSTRACT

'Prim 41' is a new and distinct variety of sweet cherry tree which is characterized by producing large kidney shaped fruits having a dark red-black color. The fruits of 'Prim 41' are firm with a good cherry flavor and a good shelf life. The fruit stems of 'Prim41' are medium thick and long and stay green during storage and shipping. 'Prim 41' produces a high yield of high-quality fruits that may be good for export markets.

4 Drawing Sheets

Latin name of the genus and species: The Latin name of the novel plant variety disclosed herein is *Prunus avium* (L.) L.

Variety denomination: The inventive variety of the *Prunus avium* (L.) L. disclosed herein has been given the varietal denomination 'Prim 41'.

BACKGROUND OF THE INVENTION

The present invention relates to a new and distinct variety of sweet cherry tree which is characterized by producing large size dark red-black fruits having a reniform shape. 'Prim 41' exhibits a middle fruit ripening time. The fruits of 'Prim 41' are medium firm with medium acid and have a pleasant cherry flavor and a strong stem attachment. 'Prim 41' fruits have good shelf-life.

The new and distinct cherry variety described and claimed herein was developed in 2007 in Baden-Wuerttemberg, Germany and originated from open pollinated seeds of fruits of the female parent 'Tieton' (U.S. Plant Pat. No. 8,051, also known as 'PC 7144-7'). The male parent is unknown. The present variety of sweet cherry plant was selected as a single plant and was first asexually propagated in 2008 by grafting on 'Gisela 5' rootstock (U.S. Plant Pat. No. 9,622, also known as GI 148-2) in Kressbronn, Baden-Wuerttemberg, Germany.

'Prim 41' is believed to be most similar to the cherry variety 'Prim 25' (U.S. Plant Pat. No. 33,719). 'Prim 41' is distinguished from 'Prim 25' (U.S. Plant Pat. No. 33,719) by at least having a fruit that is slightly more firm and a different shape than that of 'Prim 25', with 'Prim 41' having a slightly flatter shape. In addition, 'Prim 41' has a longer stem than 'Prim 25'. Both 'Prim 41' and 'Prim 25' have a good fruit size that is dark red-black in color. 'Prim 41' has the same flowering time as 'Burlat' (unpatented) but exhibits a much higher fruit firmness than 'Burlat'. In addition, 'Prim 41' has a weaker tree growth than 'Burlat'. 'Prim 41 has much darker fruit color and higher fruit firmness than 'Bellise'

(unpatented). Prim 41 has a slightly lighter fruit skin color than 'Kordia' (unpatented) and 'Satin' (unknown patent protection) and has shorter stem than 'Kordia'. 'Prim 41' has bigger fruit size than 'Chelan' (U.S. Plant Pat. No. 8,545, also known as 'PC 7146-23').

When compared to its female parent, 'Teiton', 'Prim 41' exhibits a fruit ripening time that is about 2 days later than 'Tieton'. In addition, 'Prim 41' has a different fruit shape and tree habit than 'Tieton'. Specifically, fruits of "Tieton" are broadly cordate, in comparison to "Prim 41," which has reniform shaped fruits. Growth: Tieton is vigorous and upright spreading, while Prim 41 growth is medium vigor and upright to spreading. 'Prim 41' has a dark red fruit color and firmness that is very similar to 'Tieton'.

Asexual reproduction of 'Prim 41' by grafting and budding onto rootstock shows that the foregoing and all other characteristics and distinctions described herein remain true to type and are established and transmitted through successive propagations. 'Prim 41' has not been evaluated under all possible environmental conditions. The phenotype may vary with variations in environment without a change in the genotype of the plant.

SUMMARY OF THE INVENTION

The new sweet cherry variety, 'Prim 41,' is characterized by producing large kidney shaped fruits having a dark red-black color. The fruits of 'Prim 41' ripen in about 10 days after 'Burlat', giving it a middle or medium ripening time. The fruits of 'Prim 41' are firm with a good cherry flavor and a good shelf life. 'Prim 41' produces a high yield of high-quality fruits that may be good for export markets. The fruit stems of 'Prim41' are medium thick and long and stay green during storage and shipping.

BRIEF DESCRIPTION OF THE PHOTOGRAPHS

This new cherry tree is illustrated by the accompanying photographs which show the plant's foliage and inflorescences. The colors shown are as true as can be reasonably obtained by conventional photographic procedures. Colors in the photographs may differ slightly from the color values cited in the detailed botanical description, which accurately describe the colors of the new cherry tree. The accompanying photographic drawings illustrate the new variety at approximately 7 years of age.

DETAILED BOTANICAL DESCRIPTION

Figure 1:
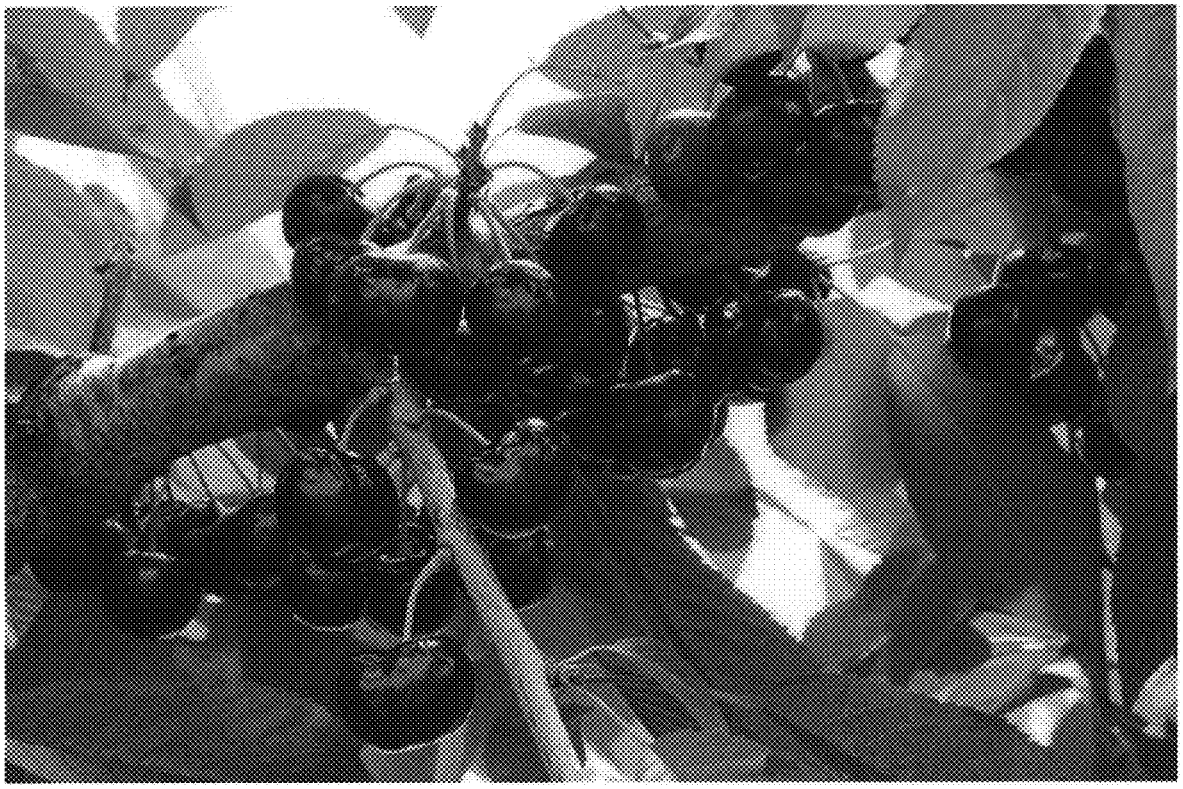
FIG. 1 is a color photograph showing typical specimens of the fruit and stem of 'Prim 41'.
Figure 2:
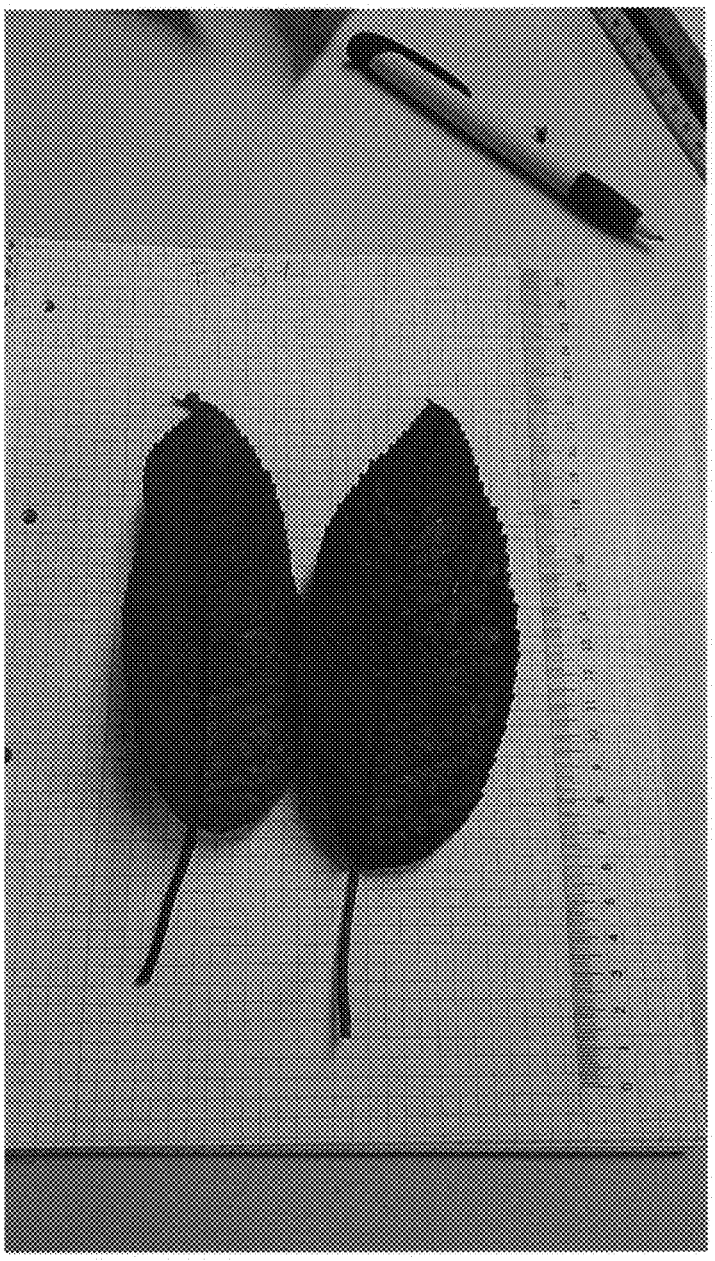
FIG. 2 is a color photograph showing the upper surface of leaves from 'Prim 41'.
Figure 3:
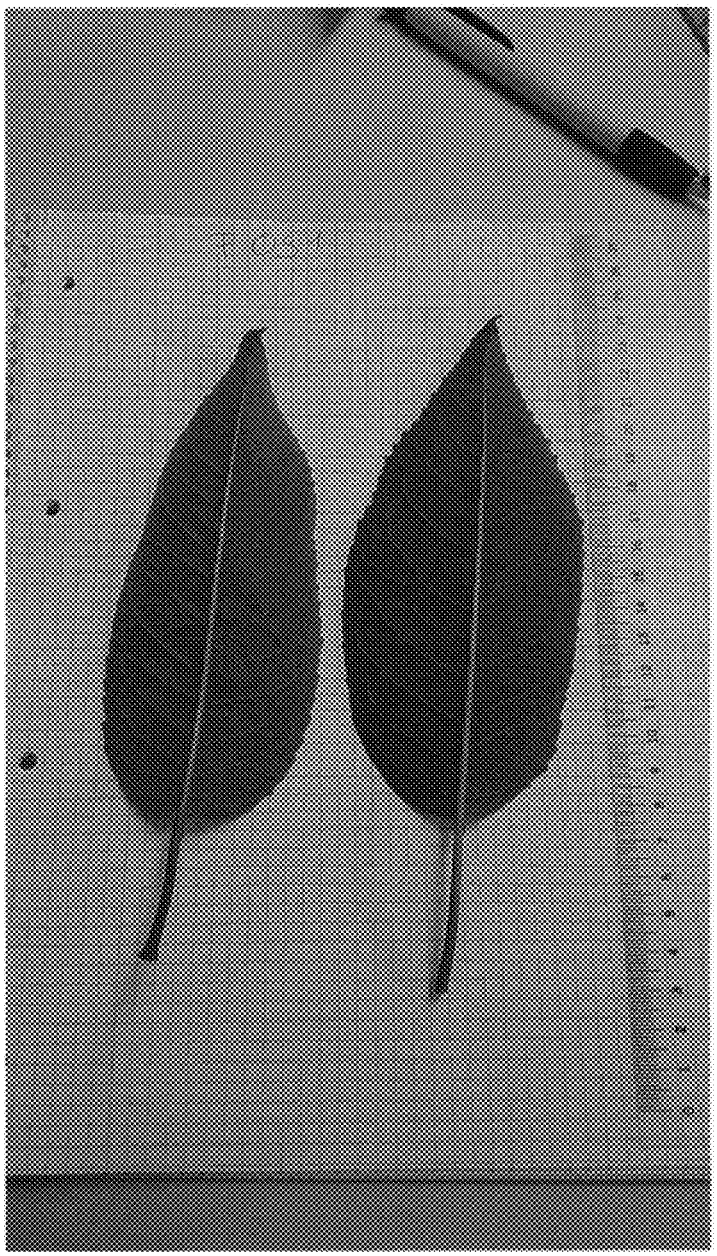
FIG. 3 is a color photograph showing the lower surface of leaves from 'Prim 41'.
Figure 4:
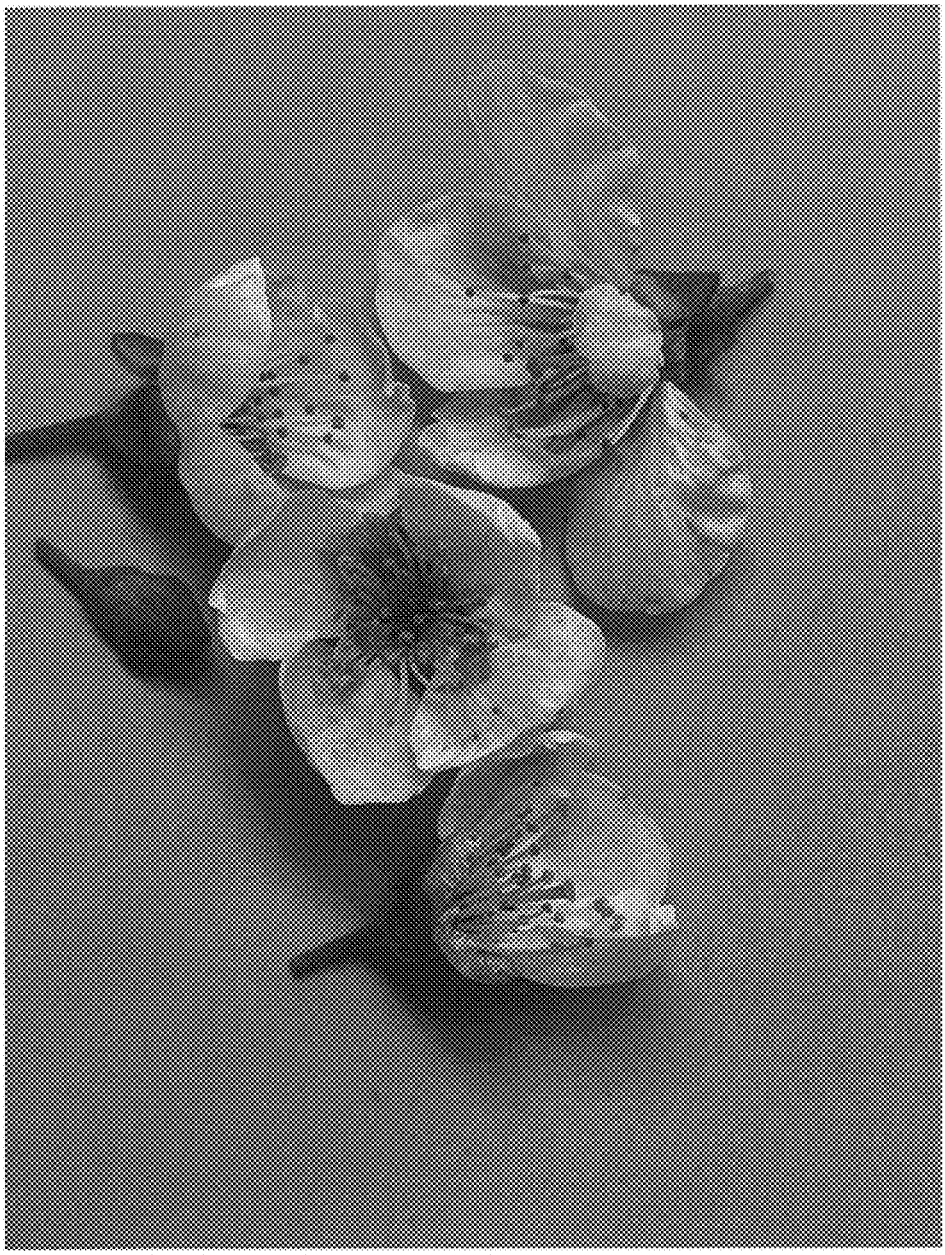
FIG. 4 is a color photograph showing the flower bud and flower of 'Prim 41'.

The following is a detailed description of the botanical characteristics of the new and distinct variety of the sweet cherry tree known by the denomination 'Prim 41'. The detailed description was taken on a seven-year-old tree in Baden-Wuerttemberg, Germany. All colors cited herein refer to The Royal Horticultural Society Mini Colour Chart (The Royal Horticultural Society (RHS), London, 2005 Edition). Where specific dimensions, sizes, colors, and other characteristics are given, it is to be understood that such characteristics are approximations or averages set forth as accurately as practicable.

Tree:

*Vigor.*—Medium.
*Height.*—3 meters.
*Width.*—2 meters.
*Growth habit.*—Spreading.
*Canopy density.*—Medium.
*Form.*—Upright to spreading.
*Trunk diameter.*—10 cm at 100 cm above ground.
*Trunk surface texture.*—Smooth with prominent lenticels. Lenticel length: about 1-2 cm. Lenticel width: about 0.5 cm. Lenticel color: Grayed Orange 167 A. Lenticel density: medium.
*Bark color.*—Dark brown 200 B.

Branches:

*Diameter.*—1.6 cm.
*Surface.*—Smooth.
*Form.*—Upright to spreading.
*Bark color.*—Brown green 152 B.
*Average angle.*—Intermediate.
*Lenticels.*—Length: approximately 0.1 cm. Width: approximately 0.1 cm. Shape: roundish. Density: medium. Color: Yellow Brown 167 B.

Leaves:

*Length.*—16.5 cm.
*Width.*—8 cm.
*Arrangement or position.*—Alternating.
*Form.*—Long, narrow.
*Texture.*—Leathery, no crisp feeling.
*Thickness.*—Medium.
*Base.*—Rounded.
*Apex.*—Narrow, short acuminate.
*Margin.*—Serrate.
*Pubescence upper surface.*—None.
*Pubescence lower surface.*—None.
*Color young leaves upper surface.*—Green 146 C.
*Color young leaves lower surface.*—Green 146 C.
*Color mature leaves upper surface.*—Dark green 137 A.
*Color mature leaves lower surface.*—Green 137 C.
*Petiole shape.*—Narrow.
*Petiole length.*—~4.3 cm.
*Petiole diameter.*—~0.3 cm.
*Petiole color.*—Green 146 C (spring)/purple brown 183 A (summer/fall).
*Venation type.*—Pinnate.
*Veins color upper surface.*—Light yellow brown 163 B.
*Veins color lower surface.*—Light yellow brown 163 B.

Flower buds:

*Length.*—0.9 cm.
*Width.*—0.5 cm.
*Color.*—Yellow green 154 B.
*Pedicel length.*—0.9 cm.
*Pedicel diameter.*—0.12 cm.
*Pedicel color.*—Yellow green 145 A.

Flowers:

*Bloom timing.*—About 40% Apr. 16, 2021 Kressbronn, Germany.
*Blooming period.*—Compact, early.
*Pollination requirements.*—S-alleles S1S3.
*Number of flowers per raceme.*—3-5, generally 4.
*Fragrance.*—None.
*Petals.*—Number — 5.
*Petals.*—Length — 1.4 cm.
*Petals.*—Width — 1.5 cm.
*Petals.*—Shape — wide, shell-shaped.
*Petals.*—Margin — repand.
*Petals.*—Texture and appearance — smooth.
*Petals.*—Color — When opening upper surface: White N 999 D. When opening lower surface: White N 999 D. Fully opened upper surface: White N 999 D. Fully opened lower surface: White N 999 D.
*Sepals.*—Shape — oval, obtuse.
*Sepals.*—Margin — entire.
*Sepals.*—Texture — smooth.
*Sepals.*—Length — 0.6 cm.
*Sepals.*—Width — 0.4 cm.
*Sepals.*—Color upper surface — dark green 144 A.
*Sepals.*—Color lower surface — dark green 144 A.
*Stamens.*—Number per flower — up to 33-38.
*Filament length.*—0.25-1 cm.
*Anthers.*—Kidney shape.
*Anthers.*—Length — 0.1 cm.
*Anthers.*—Color — yellow brown 163 B.
*Pollen color.*—Yellow brown 163 B.
*Pollen amount.*—Intermediate.
*Pistils.*—Length 1.6-1.9 cm.
*Style length.*—1.1 cm.
*Style color.*—Brown green 152 D.
*Stigma shape.*—Kidney.
*Stigma color.*—Brown green 152 D.

Fruit:

*Shape.*—Kidney.
*Diameter.*—31 mm.
*Skin color.*—Dark purple brown 187 A.
*Skin ground color.*—Dark purple brown 187 A.
*Skin thickness.*—Medium.
*Skin texture.*—Smooth.
*Skin tendency to crack.*—Medium.
*Flesh color.*—Dark pink red 53 C.
*Texture.*—Firm.
*Aroma.*—Pleasant.

*Eating quality.*—Good.
*Stone length.*—1.3 cm.
*Stone width.*—0.8 cm.
*Stone form.*—Oval.
*Stone color.*—Orange white 159 A.
*Stem length.*—41 mm.
*Stem width.*—2 mm.
*Stem color.*—Yellow green 145 B.
*Average weight.*—12.6 g.
*Ripening period middle.*—Jun. 17, 2018.
*Use.*—Fresh market and storage; brix about 18.80-18.90 Durofel; good eating quality and flavor.

Productivity depends on the density of planting but is about 14 t/ha.

Resistance to pathogens is typical of *Prunus avium* species generally.

What is claimed is:

1. A new and distinct variety of sweet cherry tree named 'Prim 41' having the characteristics substantially as described and illustrated herein.

* * * * *